US008334417B2

(12) United States Patent
Himmler

(10) Patent No.: US 8,334,417 B2
(45) Date of Patent: Dec. 18, 2012

(54) PROCESS FOR PREPARING CHLORO- AND BROMOAROMATICS

(75) Inventor: Thomas Himmler, Odenthal (DE)

(73) Assignee: Bayer Cropscience AG, Monheim (DE)

( * ) Notice: Subject to any disclaimer, the term of this patent is extended or adjusted under 35 U.S.C. 154(b) by 364 days.

(21) Appl. No.: 12/720,247

(22) Filed: Mar. 9, 2010

(65) Prior Publication Data

US 2010/0234652 A1    Sep. 16, 2010

(30) Foreign Application Priority Data

Mar. 12, 2009   (EP) .................................... 09155017

(51) Int. Cl.
    *C07C 17/00*    (2006.01)
(52) U.S. Cl. ........................ 570/208; 570/207
(58) Field of Classification Search .................. 570/207, 570/208
    See application file for complete search history.

(56) References Cited

U.S. PATENT DOCUMENTS

| 5,262,383 | A | 11/1993 | Fischer et al. |
| 6,114,374 | A | 9/2000 | Lieb et al. |
| 2007/0015664 | A1 | 1/2007 | Fischer et al. |

FOREIGN PATENT DOCUMENTS

| EP | 0 458 006 A1 | 11/1991 |
| FR | 2 475 535 A | 8/1981 |
| WO | WO 99/47525 A1 | 9/1999 |
| WO | WO 00/78712 A1 | 12/2000 |
| WO | WO 00/78881 A2 | 12/2000 |
| WO | WO 2004/050607 A1 | 6/2004 |
| WO | WO 2006/084663 A1 | 8/2006 |
| WO | WO 2008/049507 A1 * | 5/2008 |

OTHER PUBLICATIONS

Hodgson, H., et al., "An Interpretation of the Sandmeyer Reaction. Part IV. Catalysed Decomposition of Diazonium Kations by Anionoid Complexes with Special Reference to those of Cobalt and Ferric Iron," *J. Chem. Soc.*, pp. 18-19, Royal Society of Chemistry, United Kingdom (1944).
Hodgson, H. and Sibbald, D., "An Interpretation of the Sandmeyer Reaction. Part V. The Comparitive Behaviour of Cuprous, Cupric, and Ferric Chlorides as Catalysts.," *J. Chem. Soc.*, pp. 393-395, Royal Society of Chemistry, United Kingdom (1944).
Methoden der Organischen Chemie (Houben-Weyl). vol. V/3, p. 846 ff., O. Bayer, H. Meerwein, and K. Ziegler. Theime, Stuttgart (1962).
Methoden der Organischen Chemie (Houben-Weyl). vol. V/4, p. 437ff., O. Bayer, H. Meerwein, and K. Ziegler. Theime, Stuttgart (1990).
Nakatani, Y., "Reaction de Sandmeyer Par Le Chlorure Ferreux," *Tetrahedron Lett. 51*:4455-4458, Pergamon Press, United Kingdom (1970).
Sandmeyer, T., "Ueber die Ersetzung der Amid-gruppe durch Chlor, Brom und Cyan in den aromatischen Substanzen,"*Chem. Berichte 17*:2650-2653 (1884) (XP 002540175).
Schnyder, A., et al., "A Convenient Protocol for the Synthesis of Hindered Aryl Malononitriles," *Synlett*, pp. 3167-3169, Georg Thieme Verlag Stuttgart, United States (2006).
Zeevaart, J., et al., "Palladium-catalysed arylation of acetoacetate esters to yield 2-arylacetic acid esters," *Tetrahedron Letters 45*:4261-4264, Elsevier, United Kingdom (2004).
Dialog File 351, Accession No. 2179942, Derwent WPI English language abstract for FR 2 475 535 A, 1983.
International Search Report of PCT Application No. PCT/EP2010/001395, 2010.

* cited by examiner

*Primary Examiner* — Jafar Parsa
(74) *Attorney, Agent, or Firm* — Sterne, Kessler, Goldstein & Fox P.L.L.C.

(57) ABSTRACT

The present invention relates to a novel process for preparing chloro- or bromoaromatics of the formula (II) by diazotizing the formula (I) by means of sodium nitrite or potassium nitrite in the presence of aqueous hydrochloric or hydrobromic acids and then reacting with an iron(II) or iron(III) compound, optionally in the presence of additional amounts of hydrogen chloride or hydrogen bromide or alkali metal or alkaline earth metal chlorides or bromides.

13 Claims, No Drawings

PROCESS FOR PREPARING CHLORO- AND BROMOAROMATICS

The present invention relates to a novel process for preparing chloro- and bromoaromatics.

Such chloro- and bromoaromatics serve, among other uses, as starting materials for preparing 2-arylmalononitriles (Synlett 2006, 3167-9; WO 2004/050607) and phenylacetic acids (see, for example, Tetrahedron Letters 45 (2004) 4261-4). Such 2-arylmalononitriles and phenylacetic acids in turn are important intermediates for preparing compounds with acaricidal (see, for example, DE-A-4216814), insecticidal (see, for example, WO 98/5638) or herbicidal (see, for example, WO 04/80962; WO 99/47525; WO 2000/78881) action.

Chloro- and bromoaromatics can be prepared by various methods which have been known for some time. These are, for example, direct chlorination or bromination of the corresponding aromatic compounds, or the conversion of an aniline to the chlorine- or bromine-substituted aromatic compound by a Sandmeyer reaction (Houben-Weyl Vol. V/3, p. 846ff.; Houben-Weyl Vol. V/4, p. 437ff.).

The Sandmeyer reaction for preparing a chloro- or bromoaromatic from the corresponding aniline is generally performed by diazotizing the aniline in aqueous solution or suspension in the presence of hydrochloric or hydrobromic acid by means of addition of sodium nitrite or potassium nitrite, and then adding a copper(I) salt (CuCl; CuBr) to bring about the introduction of the chlorine or bromine atom with elimination of nitrogen. The copper salt can in principle also be used in a substoichiometric amount. This leads, however, to unsatisfactory yields in some cases. Methods of performing this reaction without addition of a metal salt have also become known (WO 2000/78712, Ex. P1). Likewise known is performance of this reaction in such a way that the diazotization is performed without use of water by means of an alkyl nitrite in an organic solvent. Subsequent conversion can be effected by various methods: with stoichiometric amounts of a copper salt; use of substoichiometric amounts of a copper salt and HCl or HBr gas; or in specific cases dispensing entirely with the addition of a transition metal salt (WO 2006/084663).

Since alkyl nitrites possess only a limited thermal stability, diazotization by means of sodium nitrite or potassium nitrite is preferable from a technical point of view.

Although the use of the copper salts for conversion of the diazonium compounds to the chloro- or bromoaromatics has been implemented industrially for some time, it has the disadvantage that the copper-containing wastes have to be disposed of. The copper(I) salt is generally used in stoichiometric amounts. If attempts are made to reduce the amount of copper-containing wastes by using the copper(I) chloride or bromide in a substoichiometric proportion, the reaction often forms an increased level of undesired by-products, for example the corresponding phenols as a result of boiling of the diazonium salt. Attempts have therefore also already been made to use metal salts other than copper salts to perform the Sandmeyer reaction. For example, the use of iron(III) chloride to prepare chloroaromatics has become known (J. Chemical Society 1944; 18-19; J. Chemical Society 1944; 393-5). However, the iron(III) chloride is used in superstoichiometric amounts. The use of iron(II) chloride has also become known (Tetrahedron Letters 51 (1970) 4455-8). It has likewise already become known to prepare chloroaromatics by a Sandmeyer reaction in the presence of an iron(II) salt in substoichiometric amounts, although copper(I) chloride is also used at the same time (FR-A-2475535). The problem of the copper-containing wastes has thus not been completely solved in this way.

Some of the methods which have become known to date for performing the Sandmeyer reaction for preparing chloro- or bromoaromatics accordingly have considerable inadequacies and disadvantages, in particular with regard to performance on the industrial scale.

It has now been found that the Sandmeyer reaction for preparing chloro- and bromoaromatics can advantageously be performed in such a way that, in a first step, the corresponding aniline of the formula (I) is diazotized in a known manner by means of sodium nitrite or potassium nitrite in the presence of aqueous hydrochloric or hydrobromic acid and then, in a second step, converted by addition of an iron(II) or iron(III) compound and optionally with addition of chloride- or bromide-containing compounds to the chloro- or bromoaromatics of the formula (II). The iron(II) or iron(III) compound is preferably used in substoichiometric amounts. The use of copper salts, such as copper(I) chloride, is no longer necessary.

The process according to the invention for preparing compounds of the formula (II) can be illustrated by the following scheme:

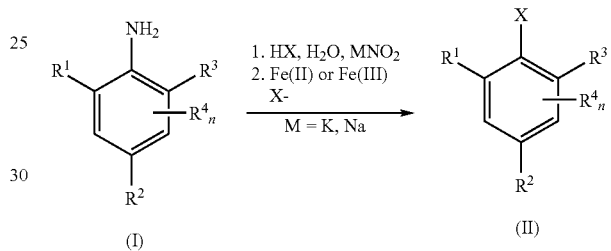

In the formulae (I) and (II),

X is chlorine or bromine, $R^1$, $R^2$ and $R^3$ are the same or different and are independently hydrogen, halogen, $C_1$-$C_6$-alkyl, $C_1$-$C_6$-haloalkyl, $C_2$-$C_6$-alkenyl, $C_2$-$C_6$-alkynyl, optionally substituted $C_3$-$C_6$-cycloalkyl or $C_4$-$C_6$-cycloalkenyl, $C_1$-$C_6$-alkoxy, $C_1$-$C_6$-haloalkoxy, optionally substituted phenyl, phenoxy, heterocyclyl or hetaryl, or cyano, $C_1$-$C_6$-alkylamino or di($C_1$-$C_6$-alkyl)amino, $R^4$ is halogen, $C_1$-$C_6$-alkyl, $C_1$-$C_6$-haloalkyl, $C_2$-$C_6$-alkenyl, $C_2$-$C_6$-alkynyl, optionally substituted $C_3$-$C_6$-cycloalkyl or $C_4$-$C_6$-cycloalkenyl, $C_1$-$C_6$-alkoxy, $C_1$-$C_6$-haloalkoxy, optionally substituted phenyl, phenoxy, heterocyclyl or hetaryl, or cyano, $C_1$-$C_6$-alkylamino or di($C_1$-$C_6$-alkyl)amino, $R^1$, $R^2$ and $R^3$ are preferably the same or different and are independently hydrogen, fluorine, chlorine, bromine, $C_1$-$C_4$-alkyl, $C_2$-$C_4$-alkenyl, $C_2$-$C_4$-alkynyl, optionally substituted cyclopropyl or cyclopentyl, $C_1$-$C_4$-alkoxy, optionally substituted phenyl or phenoxy, or cyano, $R^4$ is preferably fluorine, chlorine, bromine, $C_1$-$C_4$-alkyl, $C_2$-$C_4$-alkenyl, $C_2$-$C_4$-alkynyl, optionally substituted cyclopropyl or cyclopentyl, $C_1$-$C_4$-alkoxy, optionally substituted phenyl or phenoxy, or cyano, $R^1$, $R^2$ and $R^3$ are more preferably the same or different and are independently hydrogen, chlorine, bromine, methyl, ethyl, i-propyl, n-propyl or cyclopropyl, $R^4$ is more preferably chlorine, bromine, methyl, ethyl, i-propyl, n-propyl or cyclopropyl, $R^1$ is most preferably $C_1$-$C_4$-alkyl (with emphasis for methyl, ethyl or isopropyl), $R^2$ is most preferably hydrogen, $C_1$-$C_4$-alkyl or halogen (with emphasis for hydrogen, methyl or chlorine), $R^3$ is most preferably hydrogen or $C_1$-$C_4$-alkyl (with emphasis for hydrogen, methyl or ethyl), n is 0, 1 or 2, n is preferably 0 or 1, n is more preferably 0 or 1, n is most preferably 0.

In the definitions of the symbols given in the above formulae, collective terms were used, which are generally representative of the following substituents:

Halogen: fluorine, chlorine, bromine and iodine

Alkyl: saturated, straight-chain or branched hydrocarbon radicals having 1 to 8 carbon atoms, for example $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; heptyl, octyl.

Haloalkyl: straight-chain or branched alkyl groups having 1 to 8 carbon atoms, where some or all of the hydrogen atoms in these groups are replaced by halogen atoms as specified above, for example $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl and 1,1,1-trifluoroprop-2-yl.

Alkenyl: unsaturated, straight-chain or branched hydrocarbon radicals having 2 to 8 carbon atoms and one double bond in any position, for example $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

Alkynyl: straight-chain or branched hydrocarbon groups having 2 to 8 carbon atoms and one triple bond in any position, for example $C_2$-$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl.

Cycloalkyl: monocyclic, saturated hydrocarbon groups having 3 to 8 carbon ring members, such as cyclopropyl, cyclobutyl, cyclopentyl, cyclohexyl, cycloheptyl and cyclooctyl.

Cycloalkenyl: monocyclic, nonaromatic hydrocarbon groups having 4 to 8 carbon ring members with at least one double bond, such as cyclopenten-1-yl, cyclohexen-1-yl, cyclohepta-1,3-dien-1-yl.

Heterocyclyl/hetaryl: unsubstituted or substituted, unsaturated or fully or partly saturated heterocyclic 5- to 7-membered ring, or unsaturated or fully or partly saturated heterocyclic 3- to 8-membered ring, containing up to 4 nitrogen atoms or alternatively 1 nitrogen atom and up to 2 further heteroatoms selected from N, O and S, for example oxiranyl, aziridinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,3-dihydrothien-2-yl, 2,3-dihydrothien-3-yl, 2,4-dihydrothien-2-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl, 1-pyrrolyl, 1-pyrazolyl, 1,2,4-triazol-1-yl, 1-imidazolyl, 1,2,3-triazol-1-yl, 1,3,4-triazol-1-yl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

It is surprisingly possible by the process according to the invention to prepare the compounds of the formula (II) in better selectivity and in higher yield than by earlier known processes.

The solvents used for the reaction in the process according to the invention are water and aqueous solutions of hydrogen chloride or hydrogen bromide.

The amount of hydrogen chloride or hydrogen bromide for use for diazotization in the process according to the invention can be varied within wide limits. The amount used will be at least that needed, according to known processes, to fully diazotize the aniline of the formula (I) in the presence of sodium nitrite or potassium nitrite.

The amount of sodium nitrite or potassium nitrite for diazotization in the first step of the process is selected by known methods such that not more than just the amount needed is used, or a slight excess, which is removed again on completion of diazotization in a known manner by addition of, for example, sulphamic acid.

The diazotization can be performed in a known manner at temperatures between −20 and +60° C. Preference is given to temperatures between −10 and +30° C.

The reaction times of the first step of the process are between 1 and 6 hours.

In the second step of the process according to the invention, the diazonium salt is converted in the presence of an iron(II) or iron(III) salt to the chloro- or bromoaromatics of the formula (II).

The amount of iron(II) or iron(III) compound for use in the process according to the invention is not critical. For example, it is possible to use 0.005 to 2 mol of iron(II) or iron(III) compound per mole of aniline. Preference is given to 0.01 to 1 mol per mole of aniline. Particular preference is given to 0.05 to 0.75 mol per mole of aniline.

Examples of iron(II) or iron(III) compounds include: iron (II) sulphate, iron(III) sulphate, iron(II) chloride, iron(III) chloride, iron(II) bromide, iron(III) bromide, iron(II) fluoride, iron(III) fluoride, iron(II) acetate, iron(II) propionate, iron(II) stearate, iron(II) sulphamate, iron(II) oxalate, iron (III) oxalate, iron(III) citrate, iron(II) gluconate, iron(II) acetylacetonate, iron(III) acetylacetonate, iron(III) nitrate, iron(III) phosphate, ammonium iron(II) sulphate, ammonium iron(III) sulphate, iron(II,III) oxide and iron(III) oxide. Preference is given to iron(II) sulphate, iron(III) sulphate, iron(II) chloride, iron(III) chloride, iron(II) bromide and iron(III) bromide.

The listing of these iron compounds in each case also means the hydrate forms which exist.

It may be advantageous, over and above the hydrogen chloride or hydrogen bromide used in the diazotization, in the second step of the process according to the invention, to use additional amounts of hydrogen chloride or hydrogen bromide in order to achieve a maximum conversion of the diazonium salt to the chlorine or bromine compound.

Instead of hydrogen chloride or hydrogen bromide, it is also possible here to use alkali metal or alkaline earth metal chlorides or bromides. Examples of alkali metal or alkaline earth metal chlorides or bromides include lithium chloride, sodium chloride, potassium chloride, magnesium chloride, calcium chloride, lithium bromide, sodium bromide, potassium bromide and magnesium bromide.

Preference is given to lithium chloride, sodium chloride, potassium chloride, lithium bromide, sodium bromide and potassium bromide.

The amounts of chloride or bromide additionally used in the second step of the process according to the invention can be varied within wide limits. They are typically between 0 and 20 mol per mole of aniline of the formula (I), preferably between 0.5 and 15 mol per mole of aniline of the formula (I).

The solvent used for the second step of the process according to the invention is preferably water. The amount of water is guided by the amount and solubility of the chlorides or bromides used in each case, or results from the concentration of the aqueous hydrogen chloride or hydrogen bromide solutions used. In general, a high space-time yield will be achieved by selecting this amount of water to be as small as possible.

The second step of the process according to the invention is performed at temperatures between 20 and 120° C. Preference is given to temperatures between 30 and 100° C.

The reaction times of the second step of the process according to the invention are between 1 and 6 hours.

The process according to the invention for preparing compounds of the formula (II) is preferably configured such that the steps are performed successively without isolating the intermediate.

The preparation of compounds of the formula (II) by the process according to the invention is to be illustrated by the preparation examples which follow:

EXAMPLE 1

4-Chloro-2,6-dimethylbromobenzene

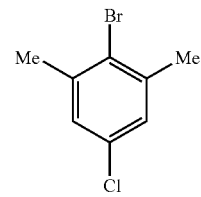

To an initial charge of 65 ml of 48% aqueous HBr are added, in portions, 15.56 g [0.1 mol] of 4-chloro-2,6-dimethylaniline. The resulting thick suspension is stirred at 80° C. for 15 minutes. It is then cooled to −10° C., and a solution of 8 g [0.116 mol] of $NaNO_2$ in 35 ml of water is added dropwise within approx. 40 minutes at such a rate that the temperature does not exceed −5° C. 80 mg of sulphamic acid are added. Then the suspension of the diazonium salt cooled to −10° C. is metered within about 25 minutes into a solution, heated to 80° C., of 28.6 g [0.103 mol] of $FeSO_4 \times 7H_2O$ in 65 ml of 62% aqueous HBr. The reaction mixture is then stirred at 80° C. for another 1 hour, allowed to cool to room temperature and admixed with 125 ml of water, the phases are separated and the aqueous phase is extracted three times with 50 ml each time of methylene chloride. The combined organic phases are washed twice with 25 ml each time of water, dried and concentrated under reduced pressure. This gives 17.2 g of an oil which, according to GC, contains 95.6% 4-chloro-2,6-dimethylbromobenzene (75% of theory).

EXAMPLE 2

4-Chloro-2,6-dimethylbromobenzene

The procedure is as in Example 1, except that only 13.9 g [0.05 mol] of FeSO$_4$×7H$_2$O are used. This gives 19.7 g of an oil which, according to GC, contains 97.7% 4-chloro-2,6-dimethylbromobenzene (87% of theory).

EXAMPLE 3

4-Chloro-2,6-dimethylbromobenzene

The procedure is as in Example 1, except that only 6.95 g [0.025 mol] of FeSO$_4$×7H$_2$O are used. This gives 20.7 g of an oil which, according to GC, contains 97.1% 4-chloro-2,6-dimethylbromobenzene (91% of theory).

EXAMPLE 4

4-Chloro-2,6-dimethylbromobenzene

The procedure is as in Example 1, except that only 3.475 g [0.0125 mol] of FeSO$_4$×7H$_2$O are used. This gives 21.5 g of an oil which, according to GC, contains 92% 4-chloro-2,6-dimethylbromobenzene (90% of theory).

EXAMPLE 5

4-Chloro-2,6-dimethylbromobenzene

The procedure is as in Example 1, except that only 1.668 g [0.006 mol] of FeSO$_4$×7H$_2$O are used. This gives 21.4 g of an oil which, according to GC, contains 84.8% 4-chloro-2,6-dimethylbromobenzene (83% of theory).

COMPARATIVE EXAMPLE 1

4-Chloro-2,6-dimethylbromobenzene

To an initial charge of 75 ml of 48% aqueous HBr are added, in portions, 19.67 g [0.12 mol] of 4-chloro-2,6-dimethylaniline. The resulting thick suspension is stirred at 80° C. for 15 minutes. Then the mixture is cooled to −10° C., and a solution of 9.6 g [0.139 mol] of NaNO$_2$ in 45 ml of water is added dropwise within approx. 1 h at such a rate that the temperature does not exceed −5° C. 100 mg of sulphamic acid are added. Then the suspension of the diazonium salt, cooled to −10° C., is metered within about 35 minutes into a solution, heated to 80° C., of 17.93 g [0.125 mol] of Cu(I)Br in 75 ml of 62% aqueous HBr. The reaction mixture is then stirred at 80° C. for another 1 hour, allowed to cool to room temperature and admixed with 125 ml of water, the phases are separated and the aqueous phase is extracted three times with 50 ml each time of methylene chloride. The combined organic phases are washed twice with 25 ml each time of water, dried and concentrated under reduced pressure. This gives 20.2 g of an oil which, according to GC, contains 95.5% 4-chloro-2,6-dimethylbromobenzene (73% of theory).

COMPARATIVE EXAMPLE 2

4-Chloro-2,6-dimethylbromobenzene

The procedure is as in Comparative Example 1, except that only 8.607 g [0.06 mol] of Cu(I)Br are used. This gives 23.6 g of an oil which, according to GC, contains 81.9% 4-chloro-2,6-dimethylbromobenzene (73% of theory).

COMPARATIVE EXAMPLE 3

4-Chloro-2,6-dimethylbromobenzene

The procedure is as in Comparative Example 1, except that only 4.304 g [0.03 mol] of Cu(I)Br are used. This gives 23.7 g of an oil which, according to GC, contains 82% 4-chloro-2,6-dimethylbromobenzene (74% of theory).

EXAMPLE 6

2,6-Diethyl-4-methylbromobenzene

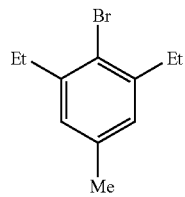

To an initial charge of 65 ml of 48% aqueous HBr are added, in portions, 16.33 g [0.1 mol] of 2,6-diethyl-4-methylaniline. The resulting thick suspension is stirred at 80° C. for 15 minutes. It is then cooled to −10° C., and a solution of 8 g [0.116 mol] of NaNO$_2$ in 35 ml of water is added dropwise within approx. 1 h at such a rate that the temperature does not exceed −5° C. 80 mg of sulphamic acid are added. Then the suspension of the diazonium salt, cooled to −10° C., is metered within about 30 minutes into a solution, heated to 80° C., of 13.9 g [0.05 mol] of FeSO$_4$×7H$_2$O in 65 ml of 62% aqueous HBr. The reaction mixture is then stirred at 80° C. for another 1 hour, allowed to cool to room temperature and admixed with 125 ml of water, the phases are separated and the aqueous phase is extracted three times with 50 ml each time of methylene chloride. The combined organic phases are washed twice with 25 ml each time of water, dried and concentrated under reduced pressure. This gives 21.3 g of an oil which, according to GC, contains 94.6% 2,6-diethyl-4-methylbromobenzene (89% of theory).

EXAMPLE 7

2,6-Diethyl-4-methylbromobenzene

The procedure is as in Example 6, except that, in the second step of the process, instead of the hydrobromic acid, a solution of 7.5 g [0.75 mol] of NaBr in 70 ml of water is used. This gives 21.9 g of an oil which, according to GC, contains 93.3% 2,6-diethyl-4-methylbromobenzene (90% of theory).

EXAMPLE 8

2,6-Dimethylbromobenzene

To an initial charge of 65 ml of 48% aqueous HBr are added, in portions, 12.12 g [0.1 mol] of 2,6-dimethylaniline.

The resulting thick suspension is stirred at 80° C. for 15 minutes. It is then cooled to −10° C., and a solution of 8 g [0.116 mol] of NaNO₂ in 35 ml of water is added dropwise within approx. 1 h at such a rate that the temperature does not exceed −5° C. 80 mg of sulphamic acid are added. Then the suspension of the diazonium salt, cooled to −10° C., is metered within about 30 minutes into a solution, heated to 80° C., of 13.9 g [0.05 mol] of FeSO₄×7H₂O in 65 ml of 62% aqueous HBr. The reaction mixture is then stirred at 80° C. for another 1 hour, allowed to cool to room temperature and admixed with 125 ml of water, the phases are separated and the aqueous phase is extracted three times with 50 ml each time of methylene chloride. The combined organic phases are washed twice with 25 ml each time of water, dried and concentrated under reduced pressure. This gives 17.4 g of an oil which, according to GC, contains 83% 2,6-dimethylbromobenzene (78% of theory).

COMPARATIVE EXAMPLE 4

2,6-Dimethylbromobenzene

To an initial charge of 125 ml of 48% aqueous HBr are added, in portions, 24.24 g [0.2 mol] of 2,6-dimethylaniline. The resulting thick suspension is stirred at 80° C. for 15 minutes. It is then cooled to −10° C., and a solution of 16 g [0.232 mol] of NaNO₂ in 70 ml of water is added dropwise within approx. 1 h at such a rate that the temperature does not exceed −5° C. 160 mg of sulphamic acid are added. Then the suspension of the diazonium salt, cooled to −10° C., is metered within about 45 minutes into a solution, heated to 60° C., of 31.6 g [0.22 mol] of Cu(I)Br in 130 ml of 62% aqueous HBr. The reaction mixture is then stirred at 80° C. for another 1 hour, allowed to cool to room temperature and admixed with 250 ml of water, the phases are separated and the aqueous phase is extracted three times with 100 ml each time of methylene chloride. The combined organic phases are washed with 50 ml each of water and saturated aqueous NaCl solution, dried and concentrated under reduced pressure. This gives 33.3 g of an oil which, according to GC, contains 75.6% of 2,6-dimethylbromobenzene (68% of theory).

EXAMPLE 9

2,6-Diethyl-4-methylchlorobenzene

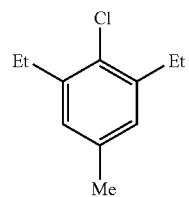

To an initial charge of 65 ml of 36% aqueous HCl are added, in portions, 16.33 g [0.1 mol] of 2,6-diethyl-4-methylaniline. The resulting thick suspension is stirred at 65° C. for 5 minutes. It is then cooled to −10° C., and a solution of 8 g [0.116 mol] of NaNO₂ in 35 ml of water is added dropwise within approx. 1 h at such a rate that the temperature does not exceed −5° C. 80 mg of sulphamic acid are added. Then the suspension of the diazonium salt, cooled to −10° C., is metered within about 30 minutes into a solution, heated to 70° C., of 13.9 g [0.05 mol] of FeSO₄×7H₂O in 65 ml of 36% aqueous HCl. The reaction mixture is then stirred at 65-75° C. for another 1 hour, allowed to cool to room temperature and admixed with 200 ml of water, the phases are separated and the aqueous phase is extracted three times with 50 ml each time of methylene chloride. The combined organic phases are washed twice with 25 ml each time of water, dried and concentrated under reduced pressure. This gives 17.3 g of an oil which, according to GC, contains 87.6% 2,6-diethyl-4-methylchlorobenzene (83% of theory).

EXAMPLE 10

2,6-Diethyl-4-methylchlorobenzene

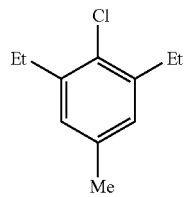

To an initial charge of 65 ml of 36% aqueous HCl are added, in portions, 16.33 g [0.1 mol] of 2,6-diethyl-4-methylaniline. The resulting thick suspension is stirred at 65° C. for 5 minutes. It is then cooled to −10° C., and a solution of 8 g [0.116 mol] of NaNO₂ in 35 ml of water is added dropwise within approx. 1 h at such a rate that the temperature does not exceed −5° C. 80 mg of sulphamic acid are added. Then the suspension of the diazonium salt, cooled to −10° C., is metered within about 30 minutes into a solution, heated to 70° C., of 8.36 g [0.05 mol] of FeCl₃ in 65 ml of 36% aqueous HCl. The reaction mixture is then stirred at 65-75° C. for another 1 hour, allowed to cool to room temperature and admixed with 200 ml of water, the phases are separated and the aqueous phase is extracted three times with 50 ml each time of methylene chloride. The combined organic phases are washed twice with 25 ml each time of water, dried and concentrated under reduced pressure. This gives 18.1 g of an oil which, according to GC, contains 89% 2,6-diethyl-4-methylchlorobenzene (88% of theory).

EXAMPLE 11

2,6-Diethyl-4-methylchlorobenzene

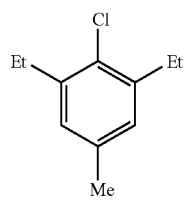

To an initial charge of 65 ml of 36% aqueous HCl are added, in portions, 16.33 g [0.1 mol] of 2,6-diethyl-4-methylaniline. The resulting thick suspension is stirred at 50° C. for 5 minutes. It is then cooled to −10° C., and a solution of 8 g [0.116 mol] of NaNO$_2$ in 35 ml of water is added dropwise within approx. 1 h at such a rate that the temperature does not exceed −5° C. 80 mg of sulphamic acid are added. Then the suspension of the diazonium salt, cooled to −10° C., is metered within about 30 minutes into a solution, heated to 65° C., of 4.18 g [0.025 mol] of FeCl$_3$ in 65 ml of 36% aqueous HCl. The reaction mixture is then stirred at 65° C. for another 1 hour, allowed to cool to room temperature and admixed with 200 ml of water, the phases are separated and the aqueous phase is extracted three times with 50 ml each time of methylene chloride. The combined organic phases are washed twice with 25 ml each time of water, dried and concentrated under reduced pressure. This gives 17.9 g of an oil which, according to GC, contains 93.1% 2,6-diethyl-4-methylchlorobenzene (91% of theory).

EXAMPLE 12

2,6-Diethyl-4-methylchlorobenzene

The procedure is as in Example 10, except that, in the second step, instead of the hydrochloric acid, a solution of 7.85 g [0.785 mol] of LiCl in 40 ml of water is used. This gives 17 g of an oil which, according to GC, contains 90.3% 2,6-diethyl-4-methylchlorobenzene (84% of theory).

EXAMPLE 13

2-Isopropylbromobenzene

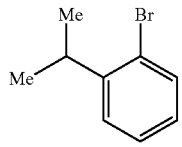

To an initial charge of 65 ml of 48% aqueous HBr are added, in portions, 13.5 g [0.1 mol] of 2-isopropylaniline. The resulting thick suspension is stirred at 80° C. for 15 minutes. It is then cooled to −10° C., and a solution of 8 g [0.116 mol] of NaNO$_2$ in 35 ml of water is added dropwise within approx. 1 h at such a rate that the temperature does not exceed −5° C. 80 mg of sulphamic acid are added. Then the thin suspension of the diazonium salt, cooled to −10° C., is metered within about 30 minutes into a solution, heated to 70° C., of 13.9 g [0.05 mol] of FeSO$_4$×7H$_2$O in 65 ml of 62% aqueous HBr. The reaction mixture is then stirred for another 1 hour without further heating and allowed to cool to room temperature, and admixed with 125 ml of water, the phases are separated and the aqueous phase is extracted three times with 50 ml each time of methylene chloride. The combined organic phases are washed twice with 25 ml each time of water, dried and concentrated under reduced pressure. This gives 18.75 g of an oil which, according to GC, contains 82.3% 2-isopropylbromobenzene (77.5% of theory).

COMPARATIVE EXAMPLE 5

2-Isopropylbromobenzene

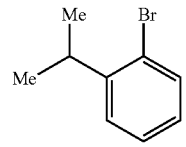

The procedure is as in Example 13, except that the reaction is performed in the presence of 7.17 g [0.05 mol] of Cu(I)Br instead of FeSO$_4$×7H$_2$O. This results in 18.2 g of an oil which, according to GC, contains 65.4% 2-isopropylbromobenzene (65.4% of theory).

The invention claimed is:
1. A process for preparing a compound of formula (II)

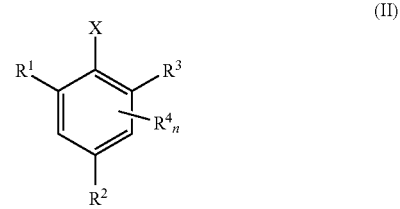

in which
X is chlorine or bromine,
R$^1$, R$^2$ and R$^3$ are the same or different and are independently hydrogen, halogen, C$_1$-C$_6$-alkyl, C$_1$-C$_6$-haloalkyl, C$_2$-C$_6$-alkenyl, C$_2$-C$_6$-alkynyl, optionally substituted C$_3$-C$_6$-cycloalkyl or C$_4$-C$_6$-cycloalkenyl, C$_1$-C$_6$-alkoxy, C$_1$-C$_6$-haloalkoxy, optionally substituted phenyl, phenoxy, heterocyclyl or hetaryl, or cyano, C$_1$-C$_6$-alkylamino or di(C$_1$-C$_6$-alkyl)amino,
R$^4$ is halogen, C$_1$-C$_6$-alkyl, C$_1$-C$_6$-haloalkyl, C$_2$-C$_6$-alkynyl, C$_2$-C$_6$ alkynyl, optionally substituted C$_3$-C$_6$-cycloalkyl or C$_4$-C$_6$-cycloalkenyl, C$_1$-C$_6$-alkoxy, C$_1$-C$_6$-haloalkoxy, optionally substituted phenyl, phenoxy, heterocyclyl or hetaryl, or cyano, C$_1$-C$_6$-alkylamino or di(C$_1$-C$_6$-alkyl)amino, and
n is 0, 1 or 2, characterized in that a compound of the formula (I):

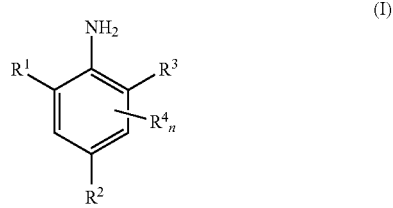

in which R$^1$, R$^2$, R$^3$, R$^4$ and n are each as defined above, is diazotized by means of sodium nitrite or potassium nitrite in the presence of aqueous hydrochloric acid or hydrobromic acid, and then converted by addition of a substoichiometric amount of an iron(II) or iron(III) compound and optionally additional amounts of hydrogen chloride or hydrogen bromide or an alkali metal or alkaline earth metal chloride or bromide.

2. The process for preparing the compound of formula (II) according to claim 1, in which
X is chlorine or bromine,
$R^1$, $R^2$ and $R^3$ are the same or different and are independently hydrogen, halogen, $C_1$-$C_6$-alkyl, $C_1$-$C_6$-haloalkyl, $C_2$-$C_6$-alkenyl, $C_2$-$C_6$-alkynyl, optionally substituted $C_3$-$C_6$-cycloalkyl or $C_4$-$C_6$-cycloalkenyl, $C_1$-$C_6$-alkoxy, $C_1$-$C_6$-haloalkoxy, optionally substituted phenyl, phenoxy, heterocyclyl or hetaryl, or cyano, $C_1$-$C_6$-alkylamino or di($C_1$-$C_6$-alkyl)amino,
$R^4$ is halogen, $C_1$-$C_6$-alkyl, $C_1$-$C_6$-haloalkyl, $C_2$-$C_6$-alkenyl, $C_2$-$C_6$-alkynyl, optionally substituted $C_3$-$C_6$-cycloalkyl or $C_4$-$C_6$-cycloalkenyl, $C_1$-$C_6$-alkoxy, $C_1$-$C_6$-haloalkoxy, optionally substituted phenyl, phenoxy, heterocyclyl or hetaryl, or cyano, $C_1$-$C_6$-alkylamino or di($C_1$-$C_6$-alkyl)amino, and n is 0 or 1.

3. The process for preparing the compound of formula (II) according to claim 1, in which
X is chlorine or bromine,
$R^1$, $R^2$ and $R^3$ are the same or different and are independently hydrogen, fluorine, chlorine, bromine, $C_1$-$C_4$-alkyl, $C_2$-$C_4$-alkenyl, $C_2$-$C_4$-alkynyl, optionally substituted cyclopropyl or cyclopentyl, $C_1$-$C_4$-alkoxy, optionally substituted phenyl or phenoxy, or cyano,
$R^4$ is fluorine, chlorine, bromine, $C_1$-$C_4$-alkyl, $C_2$-$C_4$-alkenyl, $C_2$-$C_4$-alkynyl, optionally substituted cyclopropyl or cyclopentyl, $C_1$-$C_4$-alkoxy, optionally substituted phenyl or phenoxy, or cyano, and
n is 0.

4. The process for preparing the compound of formula (II) according to claim 1, in which
X is chlorine or bromine,
$R^1$, $R^2$ and $R^3$ are the same or different and are independently hydrogen, chlorine, bromine, methyl, ethyl, i-propyl, n-propyl or cyclopropyl,
$R^4$ is chlorine, bromine, methyl, ethyl, i-propyl, n-propyl or cyclopropyl, and
n is 0 or 1.

5. The process for preparing the compound of formula (II) according to claim 1, in which
X is chlorine or bromine,
$R^1$ is $C_1$-$C_4$-alkyl,
$R^2$ is hydrogen, $C_1$-$C_4$-alkyl or halogen,
$R^3$ is hydrogen or $C_1$-$C_4$-alkyl, and
n is 0.

6. The process according to claim 1, characterized in that the iron(II) or iron(III) compound is used in amounts of 0.01 to 1 mol per mole of aniline of the formula (I).

7. The process according to claim 1, characterized in that the iron(II) or iron(III) compound is used in amounts of 0.05 to 0.75 mol per mole of aniline of the formula (I).

8. The process according to claim 1, characterized in that the iron compound used is iron(II) sulphate, iron(III) sulphate, iron(II) chloride, iron(III) chloride, iron(II) bromide, iron(III) bromide, iron(II) fluoride, iron(III) fluoride, iron(II) acetate, iron(II) propionate, iron(II) stearate, iron(II) sulphamate, iron(II) oxalate, iron(III) oxalate, iron(III) citrate, iron (II) gluconate, iron(II) acetylacetonate, iron(III) acetylacetonate, iron(III) nitrate, iron(III) phosphate, ammonium iron(II) sulphate, ammonium iron(III) sulphate, iron(II,III) oxide, iron(III) oxide or, where they exist, the particular hydrates thereof.

9. The process according to claim 8, characterized in that the iron compound used is iron(II) sulphate, iron(III) sulphate, iron(II) chloride, iron(II) chloride, iron(II) bromide, iron(III) bromide or, where they exist, the particular hydrates thereof.

10. The process according to claim 1, characterized in that an alkali metal or alkaline earth metal chloride or bromide is used in the second step.

11. The process according to claim 10, characterized in that lithium chloride, sodium chloride, potassium chloride, magnesium chloride, calcium chloride, lithium bromide, sodium bromide, potassium bromide or magnesium bromide is used.

12. The process according to claim 1, characterized in that hydrogen chloride or hydrogen bromide is used in the second step.

13. The process according to any one of claim 1 to 5 or 6-12, wherein copper salts are not used.

* * * * *